(12) United States Patent
Stroik, Jr.

(10) Patent No.: US 10,046,062 B2
(45) Date of Patent: Aug. 14, 2018

(54) RETRACTOR

(71) Applicant: TK Holdings Inc., Auburn Hills, MI (US)

(72) Inventor: Gary Lee Stroik, Jr., Swartz Creek, MI (US)

(73) Assignee: JOYSON SAFETY SYSTEMS ACQUISITION LLC, Auburn Hills, MI (US)

( * ) Notice: Subject to any disclaimer, the term of this patent is extended or adjusted under 35 U.S.C. 154(b) by 1131 days.

(21) Appl. No.: 13/655,219

(22) Filed: Oct. 18, 2012

(65) Prior Publication Data

US 2013/0140390 A1    Jun. 6, 2013

Related U.S. Application Data

(60) Provisional application No. 61/550,231, filed on Oct. 21, 2011.

(51) Int. Cl.
*A61K 38/02* (2006.01)
*A61K 47/48* (2006.01)
*B60R 22/34* (2006.01)
*B60R 22/28* (2006.01)

(52) U.S. Cl.
CPC ........ *A61K 47/48892* (2013.01); *A61K 38/02* (2013.01); *B60R 22/3413* (2013.01); *B60R 2022/286* (2013.01); *B60R 2022/289* (2013.01)

(58) Field of Classification Search
CPC ... B60R 22/28; B60R 22/341; B60R 22/4676; B60R 2022/286; B60R 2022/287
USPC ....... 242/379.1, 372, 373; 280/806; 297/470
See application file for complete search history.

(56) References Cited

U.S. PATENT DOCUMENTS

| | | | | |
|---|---|---|---|---|
| 4,323,205 | A | * | 4/1982 | Tsuge et al. ............... 242/379.1 |
| 5,618,006 | A | * | 4/1997 | Sayles ....................... 242/379.1 |
| 6,216,972 | B1 | * | 4/2001 | Rohrle ....................... 242/379.1 |
| 6,592,064 | B2 | * | 7/2003 | Clute et al. ................ 242/379.1 |
| 6,669,133 | B2 | | 12/2003 | Palliser et al. |
| 6,969,022 | B2 | * | 11/2005 | Bell et al. .................. 242/379.1 |
| 7,152,824 | B2 | * | 12/2006 | Shiotani et al. ........... 242/379.1 |
| 2010/0116921 | A1 | | 5/2010 | Gray |

* cited by examiner

*Primary Examiner* — Sang K Kim
(74) *Attorney, Agent, or Firm* — Gordon Rees Scully Mansukhani, LLP (57) ABSTRACT

A retractor assembly comprising a spool configured to wind and unwind the webbing, a lock base, and an energy absorbing member having a first end operatively connected to the locking base and a second end operatively connected to the spool. The energy absorbing member provides a progressive level of load resistance upon relative rotation between the spool and the locking base.

20 Claims, 10 Drawing Sheets

RETRACTOR

CROSS-REFERENCE TO RELATED PATENT APPLICATIONS

This application claims the benefit of and priority to U.S. Provisional Patent Application No. 61/550,231, which was filed on Oct. 21, 2011. U.S. Provisional Patent Application No. 61/550,231 is incorporated by reference herein in its entirety.

BACKGROUND

The present application relates generally to the field of retractors for use in occupant restraint systems (e.g., seatbelt systems). More specifically, the present application relates to retractors being configured with a load limiting device to provide energy management.

Figure 2:
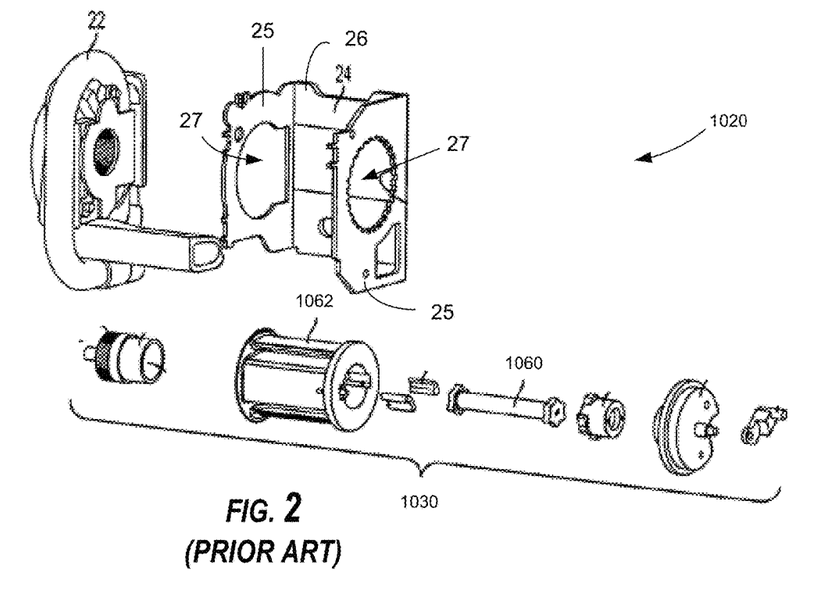
FIG. 2 is an exploded view of a conventional retractor having a torsion bar integrated within the spool.
Figure 3:
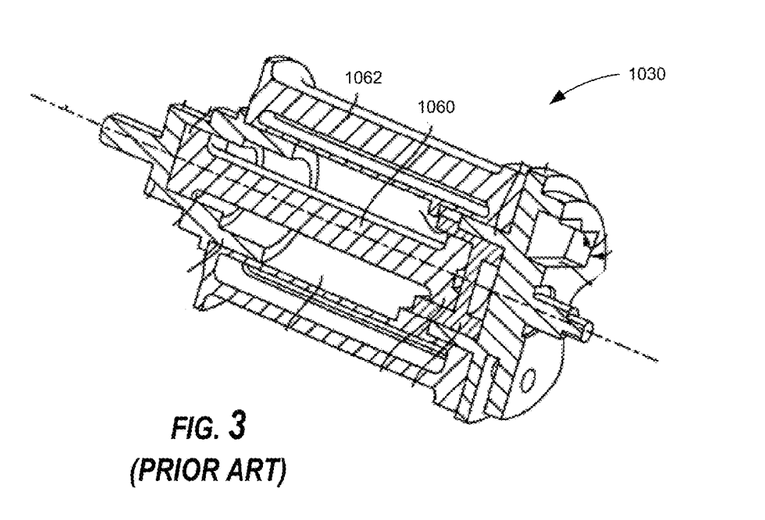
FIG. 3 is a cross-sectional view of the conventional spool of FIG. 2.
Figure 21:
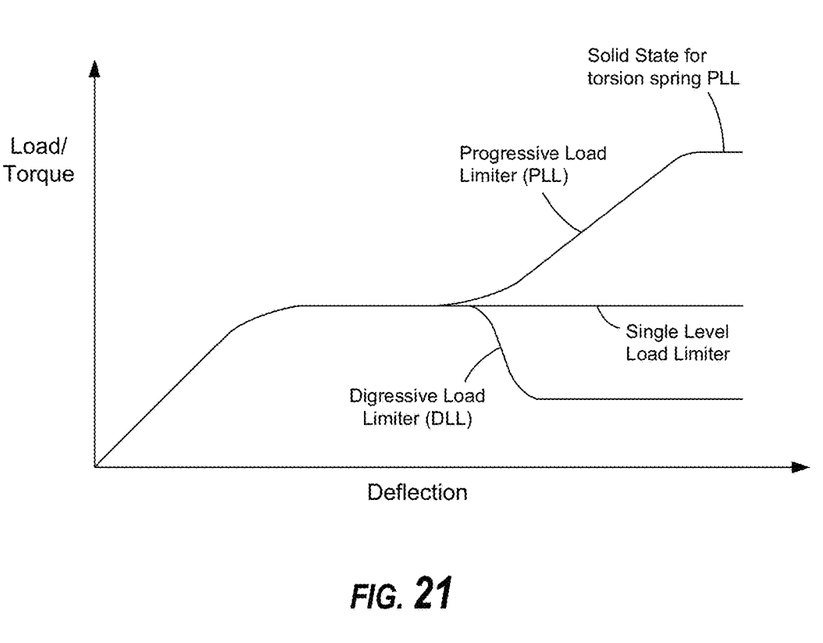
FIG. 21 is a graph showing the load over the deflection for several embodiments of retractors having various configurations.

As shown in FIGS. 2 and 3, conventional retractors 1020 commonly utilize a torsion bar 1060 disposed within the spool 1062 of the retractor 1020 to provide energy management with the purpose of removing energy from the system during a dynamic vehicle event, such as a front-impact event. The torsion bar 1060 is generally made from steel to provide a constant load throughout their design range. As a result, the load management capability of the conventional retractor 1020 is limited to a single level of energy absorption, such as shown in FIG. 21, that compares a single level load limiter (e.g., a retractor having just a torsion bar) to a retractor disclosed below that includes a progressive load limiting device.

The National Highway Traffic Safety Administration (NHTSA) has recently amended its criteria for evaluating passenger vehicles under its New Car Assessment Program (NCAP). Previously, the NCAP evaluation was based on, among other things, the acceleration of the occupant (i.e., the number of G's or g-forces that the occupant was subjected to during the dynamic event). Accordingly, it was advantageous to provide a single level load limiter to thereby limit the acceleration of the occupant during dynamic vehicle events. Now, the NCAP evaluation is based on, among other things, the chest deflection (or displacement) and compression of the occupant during the dynamic vehicle event. Accordingly, it is now desirable to provide occupant restraint systems with energy management devices that limit the chest deflection (or displacement) and compression of the occupant during such events.

SUMMARY

According to one embodiment, a seat belt retractor is provided that includes a spool configured to wind and unwind a seat belt webbing, a locking base, and an energy absorbing member having a first end operatively connected to the locking base and a second end operatively connected to the spool; wherein the energy absorbing member provides a progressive level of load resistance upon relative rotation between the spool and the locking base. The seat belt retractor may also include a case disposed between the locking base and the spool, the case being operatively coupled to the locking base and configured to house the energy absorbing member. The seat belt retractor may also include a torsion bar configured to transfer torque between the spool and the operatively coupled locking base and case, wherein the torsion bar provides a first level of load resistance and the energy absorbing member provides a second progressive level of load resistance upon relative rotation between the spool and the locking base.

Another embodiment relates to a retractor assembly for a seatbelt system having a webbing for restraining a secured occupant. The retractor includes a spool configured to wind and unwind the webbing, a lock base, and an energy absorbing member having a first end operatively connected to the locking base and a second end operatively connected to the spool. The energy absorbing member provides a progressive level of load resistance upon relative rotation between the spool and the locking base.

Another embodiment relates to a retractor assembly for a seatbelt system having a webbing for restraining a secured occupant. The retractor includes a spool configured to wind and unwind the webbing, a lock base, a shaft having a first end operatively connected to the locking base and a second end operatively connected to the spool, and an energy absorbing member having a first end operatively connected to the locking base and a second end operatively connected to the shaft. The energy absorbing member provides a progressive level of load resistance upon relative rotation between the spool and locking base.

Yet another embodiment relates to a retractor assembly for a seatbelt system having a webbing for restraining a secured occupant. The retractor includes a spool configured to wind and unwind the webbing, a lock base, a first energy absorbing member having a first end operatively connected to the locking base and a second end operatively connected to the spool, and a second energy absorbing member having a first end operatively connected to the locking base and a second end operatively connected to the first energy absorbing member. Upon relative rotation between the spool and locking base, the first energy absorbing member provides a first level of load resistance and the second energy absorbing member provides a progressive level of load resistance.

DETAILED DESCRIPTION

Disclosed herein are retractor mechanisms (e.g., retractors) that are configured to include energy management devices that absorb energy and load in a progressive manner, such as by starting off with a relative lower level of energy absorption (e.g., load resistance), then as the occupant that is secured by the webbing displaces (e.g., deflects) the retractor increases the level of load and energy absorption (e.g., load resistance). The occupant restraint systems having retractors with energy management devices (e.g., load absorbing members), as disclosed herein, are configured to limit the chest deflection (or displacement) and compression of the occupant. By initially providing a relative low level of energy absorption, the retractors, as disclosed herein, may advantageously provide improved performance for small occupants (e.g., fifth percentile occupants). Also, by providing a progressive level of load and energy absorption, the refractors, as disclosed herein, are able to restrain larger occupants (e.g., ninety-fifth percentile occupants) to limit their deflection, since the relative lower level of energy absorption ideal for smaller occupants may not be ideal to limit the deflection of the larger occupants during vehicle dynamic events. In other words, the retractors, as disclosed herein, may advantageously provide an efficient method for limiting the deflection of occupants that range in size (e.g., from small to large occupants) to provide favorable performance in view of the new NCAP criteria, such as by employing an energy management system that provides a progressive manner of load and energy absorption during dynamic vehicle events.

Figure 1:
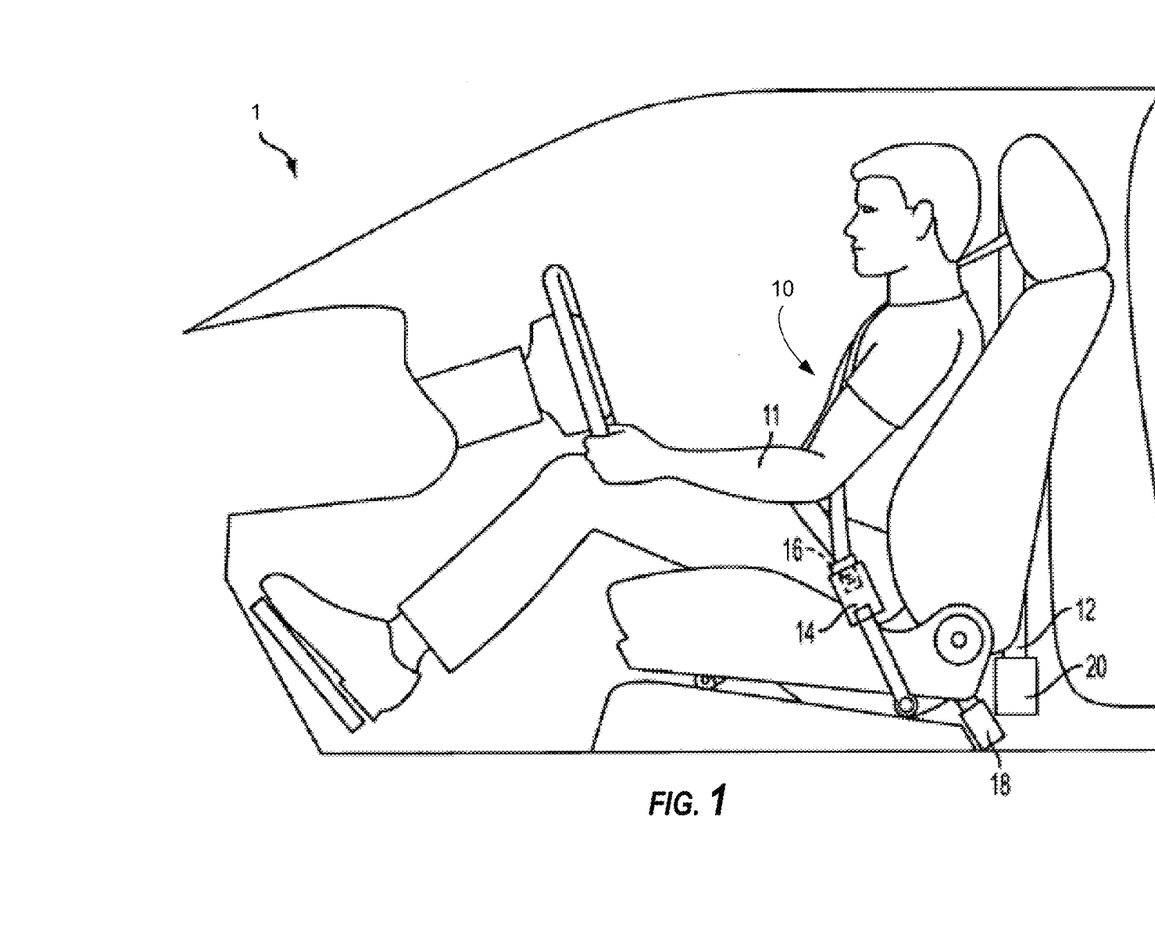
FIG. 1 is a side view of a vehicle showing an occupant restraint system in the form of a seatbelt assembly having a retractor according to an exemplary embodiment.

FIG. 1 illustrates an active occupant restraint system in the form of a seatbelt system 10. The seatbelt system 10 is used in a vehicle 1 to restrain the movement of the secured occupant 11 during a sudden positive or negative acceleration (e.g., a deceleration), such as an acceleration induced by a dynamic impact of the vehicle. The seatbelt system 10 includes a seat belt or webbing 12, a buckle mechanism 14, a tongue member 16 configured to selectively engage the buckle mechanism 14, an anchor member 18 to fix an end (e.g., a first end) of the webbing 12, and a refractor mechanism 20 (e.g., refractor assembly, retractor, etc.). Another end (e.g., a second end) of the webbing 12 is operatively coupled to the retractor 20, such that the webbing 12 is able to wind (e.g., retract) and/or unwind (e.g., extract) with respect (e.g., relative) to the refractor 20.

The retractor 20 may, for example, be configured to operate in one of two modes of operation: a first free mode of operation where the webbing 12 is able to freely wind and unwind relative to the retractor 20, such as to allow the occupant 11 to be comfortably secured in the seat by allowing extraction of the webbing to increase the slack between the occupant and the webbing; and a second energy absorbing (or locked) mode of operation where the webbing 12 may be retracted into the retractor, but the extraction of the webbing from the retractor is resisted by one or more than one energy management device (e.g., an energy absorbing member, a load absorbing member, etc.). Accordingly, during a vehicle dynamic impact event, the retractor 20 may switch from the first mode of operation to the second mode of operation to lock the retractor to thereby prohibit the webbing 12 from extracting or unwinding from the retractor 20 to prohibit deflection of the secured occupant.

The seatbelt system 10 may include one or more sensors (not shown) that detect a sudden acceleration of the vehicle, such as during a vehicle dynamic impact event. The sensor may communicate a signal to a controller (not shown) indicating the severity of the acceleration (e.g., low, high), whereby the controller may determine whether to activate the refractor 20, such as to switch the retractor 20 from the first mode of operation to the second mode of operation.

The retractor 20 may include a pretensioner, such as the pretensioner 22 shown in FIG. 2, to provide non-reversible retraction of the webbing 12 into the retractor 20, upon deployment, such as during a vehicle dynamic impact event. The pretensioner 22 retracts the webbing 12 into the retractor 20 to remove slack (e.g., clearance, looseness) between the occupant 11 and the webbing 12. The pretensioner 22 is non-reversible to prohibit extraction of the webbing 12 from the refractor 20 following retraction of the webbing 12 into the retractor 20.

Figure 4:
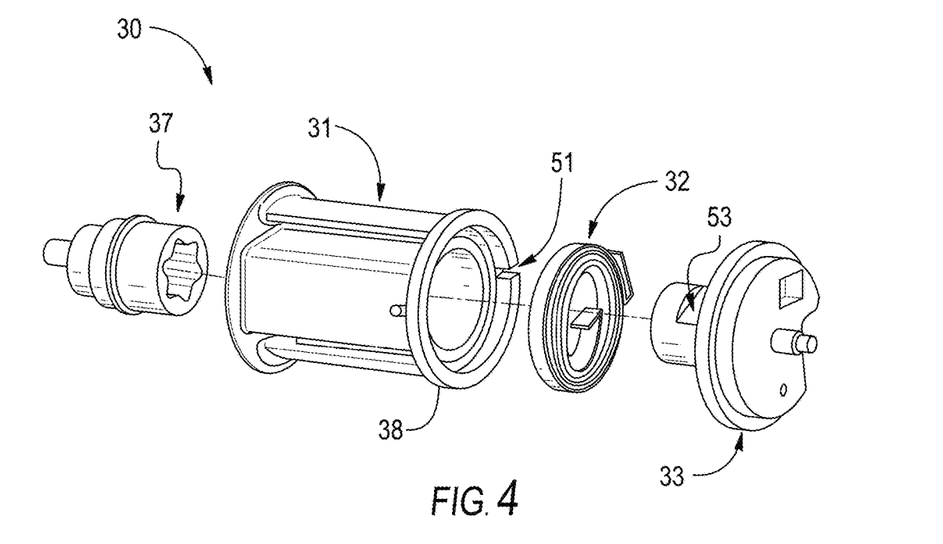
FIG. 4 is an exploded perspective view of an exemplary embodiment of a load limiting assembly for use in a retractor of an occupant restraint system.

The retractor 20 includes a frame, such as the frame 24 shown in FIG. 2, that is configured to structurally support the retractor 20 to withstand the stresses imparted to the retractor 20 from the webbing 12 induced by occupant loading during a sudden acceleration. The frame 24 is configured to pivotally support a spool assembly, such as a spool assembly 30 as shown in FIG. 4. The frame 24 includes two legs 25 that extend from a base 26, where each leg 25 includes an opening or aperture 27 that is configured to receive a portion of the spool assembly, such as the spool assembly 30.

FIGS. 4-8A illustrate an exemplary embodiment of the spool assembly 30 that is configured to provide progressive load limiting characteristics (e.g., energy absorption) to the retractor 20. As shown, the spool assembly 30 includes a spool 31, an energy absorbing member 32 (e.g., a load absorbing member, a load limiter, etc.), and a locking member 33. The retractor 20 and/or the spool assembly 30 is configured to operate in at least two modes, such as, for example, a first free mode of operation and a second energy absorbing mode of operation. When configured in the first mode of operation (e.g., free mode), the webbing 12 is able to be freely extracted and retracted from the retractor 20 about the spool 31, as the spool 31 and locking member 33 may freely rotate. When configured in the second mode of operation (e.g., energy absorbing mode), the webbing 12 is able to be freely refracted (e.g., wound) into the retractor 20, such as to pretension the webbing 12, but the extraction of the webbing 12 is resisted through the energy absorbing member 32. In other words, when the retractor 20 is configured in the energy absorbing mode of operation, the retractor 20 progressively increases the amount of load and energy absorbed by the energy absorbing member 32 as more webbing 12 is extracted from the retractor 20. Thus, the retractor 20 having the spool assembly 30 may advantageously provide progressive load limiting and/or energy absorption.

The spool 31 is configured to receive (e.g., operatively couple) an end of the webbing 12, and may be pivotally supported by the frame 24 to allow the spool 31 to rotate relative to the frame 24 in both rotational directions (e.g., clockwise and counter-clockwise) to wind (e.g., retract) and unwind (e.g., extract) the webbing 12 from the retractor 20. The spool 31 includes an annular body 36 configured to receive the end of the webbing 12. The spool 31 also includes a first end 37 configured to pivotally engage the frame 24 (e.g., the aperture 27) and a second end 38 configured to house the energy absorbing member 32. It is noted that although FIGS. 4-6A depict the first end 37 as a separate component from the body 36, the first end 37 may be integrally formed with the body 36 to form a one-piece spool 31.

According to an exemplary embodiment, the locking member 33 is pivotally coupled to the second end 38 of the spool 31, such as to retain the energy absorbing member 32 between the locking member 33 and the spool 31. As shown in the exemplary embodiment of FIG. 5, the locking member 33 is coupled to the second end 38 through a press-fit configuration retaining the energy absorbing member 32 therebetween. The locking member 33 may also be pivotally coupled to the frame 24 and/or configured to be selectively engaged by an actuator (not shown), such as a locking pawl, to prevent rotation of the locking member 33 relative to the frame 24. The locking member 33 is configured to operate in two modes of operation, a first free mode of operation and a second energy absorbing mode of operation, which correspond to the two modes of operation of the retractor 20. When in the first mode of operation (e.g., free mode), the actuator does not engage the locking member 33 and the locking member 33 is allowed to freely rotate relative to the frame and may rotate substantially in unison with the spool 31. When in the second mode of operation (e.g., the energy absorbing mode of operation), the actuator is activated to thereby engage and lock the locking member 33 to prevent rotation of the locking member 33 relative to the frame 24. In the second mode of operation, the spool 31 is allowed to rotate in the webbing extracting direction relative to the locking member 33 only as energy is absorbed by the energy absorbing member 32.

Figure 5:
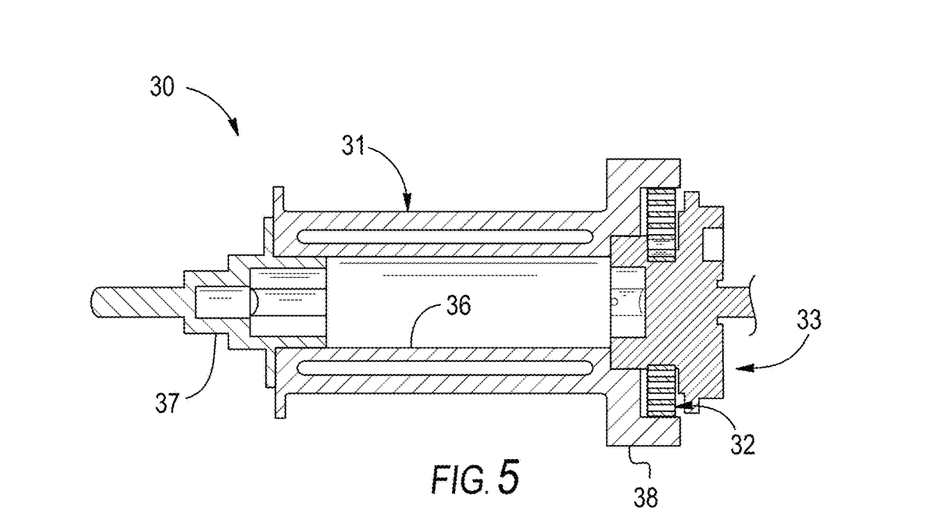
FIG. 5 is a cross-sectional view of the load limiting assembly of FIG. 4.
Figures 6, 6A, 7, 7A, 8, 8A:
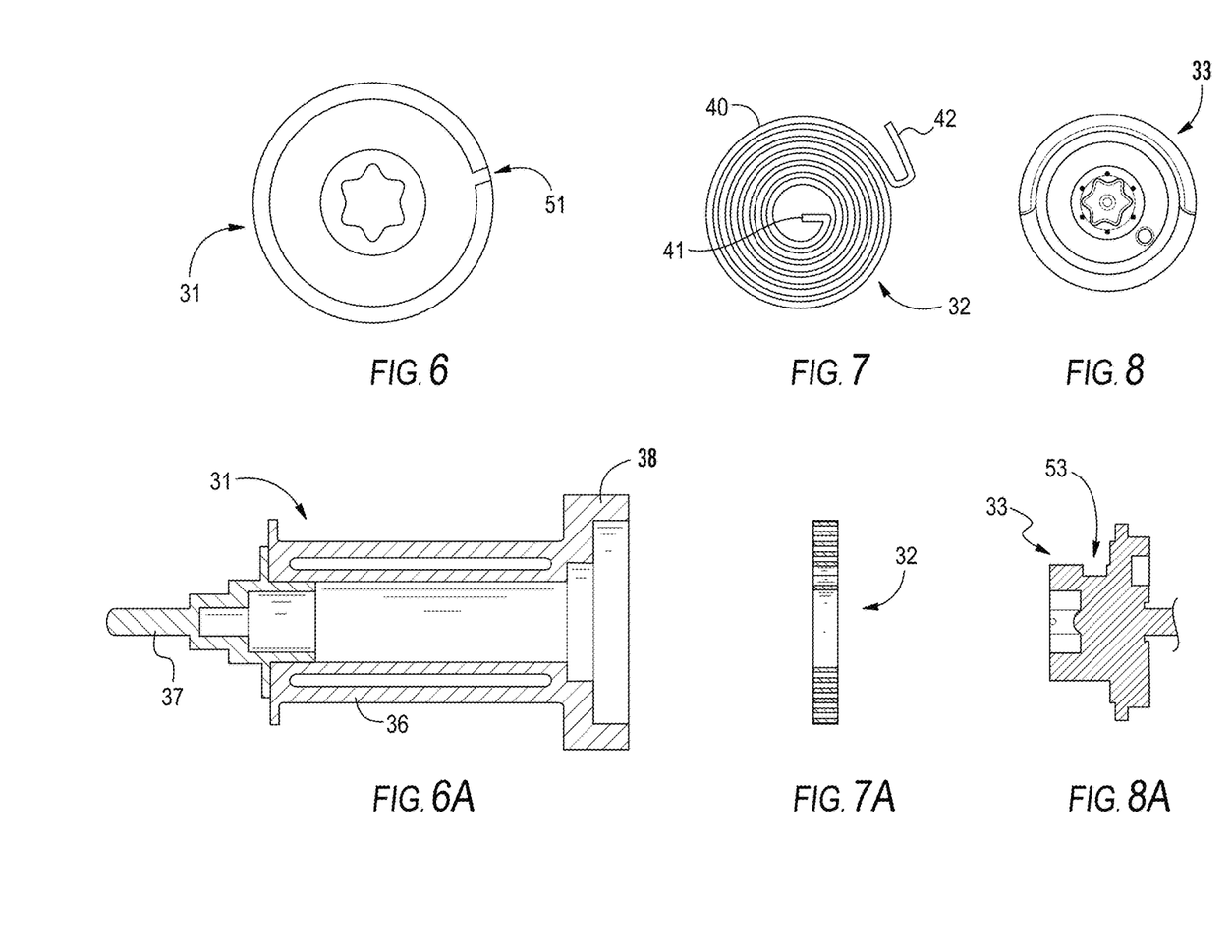
FIG. 6 is a side view of the spool of the load limiting assembly of FIG. 4.
FIG. 6A is a cross-sectional view of the spool of FIG. 6.
FIG. 7 is a side view of a load or energy absorbing member of the load limiting assembly of FIG. 4.
FIG. 7A is a cross-sectional view of the energy absorbing member of FIG. 7.
FIG. 8 is a side view of the locking member of the load limiting assembly of FIG. 4.
FIG. 8A is a cross-sectional view of the locking member of FIG. 8.

The energy absorbing member 32 is disposed between the spool 31 and the locking member 33 upon assembly, and is configured to absorb energy and load, such as energy imparted to the webbing 12 from the occupant 11 during a sudden vehicle acceleration. As shown in FIGS. 4 and 5, the energy absorbing member 32 is in the form of a torsion spring 32 that is configured to absorb energy in a progressive manner from a threshold level as the spring 32 is wound (or unwound). As shown in FIG. 7, the spring 32 includes a body 40 in the form of a coil that absorbs energy (e.g., torque), a first tang or end 41, and a second tang or end 42. As shown, the first end 41 extends from an end of the body 40 that is centrally located, and the second end 42 extends from an end of the body 40 that is located on the periphery of the body 40. The spring 32 is configured to provide energy absorption as the spring 32 is wound or unwound (i.e., one end is rotated relative to the other end), whereby the level of energy absorption is a function of the spring rate of the spring 32, which is a function of the rotational travel of one end relative to the other end. In other words, the energy absorbing member configured as a torsion spring 32 begins absorbing energy when subjected to a threshold torque that thereby winds the spring 32, then as the spring 32 is further wound the level of energy absorption increases progressively. Accordingly, the energy absorbing member 32 advantageously provides a variable rate of load and energy absorption. It is noted that the energy absorbing member configured as a torsion spring may provide energy absorption when wound or when unwound, and the retractors as disclosed herein may be configured accordingly. It is also noted that the energy absorbing member 32 may be configured differently than a torsion spring, and may still advantageously absorb or transfers energy and/or load, such as mechanical energy, in a progressive manner.

The locking member 33 may include a retention feature configured to retain a portion the energy absorbing member 32, and the spool 31 may include a retention feature configured to retain another portion of the energy absorbing member 32, such that rotation of the spool 31 relative to the locking member 33 (e.g., when the retractor is configured in the energy absorbing mode of operation) thereby transfers load and energy into the energy absorbing member 32. For example, for the energy absorbing member 32 configured as a spring 32, the first end 41 of the spring 32 may be retained by the retention feature 53 of the locking member 33 and the second end 42 of the spring 32 may be retained by the retention feature 51 of the spool 31.

As shown in FIGS. 4 and 6, the retention feature 51 of the spool 31 is configured as a notch (e.g., channel) that is configured to receive the second end 42 (e.g., the outer tang) of the energy absorbing member 32. The retention feature 51 in the form of the notch may be provided on the second end 38 of the spool 31, such that the notch is cut into an end wall of the second end 38. A portion of the spring 32 may be inserted into the notch to fix the second end 42 to the spool 31, such that rotation of the spool 31 results in movement of the second end 42 by a corresponding amount.

As shown in FIGS. 4 and 8A, the retention feature 53 of the locking member 33 is configured as an undercut portion in a shoulder of the locking member 33. The shoulder may have a circular shape, such that the undercut portion and the shoulder may form a D-shaped retention feature 51 that is configured to retain the first end 41 (e.g., inner tang) of the spring 32. The inner coil of the spring 32 may be configured to wrap around the shoulder of the locking member 33 to further help retain the spring 32 in place. Thus, the first end 41 is fixed to the locking member 33 by the retention feature 53, such that rotation of the locking member 33 results in movement of the first end 41 by a corresponding amount. Additionally, when the locking member 33 is locked to prevent rotation of the locking member 33, the first end 41 of the spring 32 is held in place, such that rotation of the spool 31 relative to the locking member 33 may induce a corresponding movement of the second end 42 relative to the first end 41.

The retention features 51, 53 may have other suitable configurations to retain the energy absorbing member 32 in a manner to allow the energy absorbing member 32 to absorb energy (e.g., load), such as when the spool 31 rotates relative to the locking member 33. For example, the retention feature 51 of the spool 31 may be in the form of an extension (e.g., a projection, a tab, a post, etc.) that is configured to retain a portion (e.g., the second end 42) of the energy absorbing member 32. Also, for example, the retention feature 53 may be in the form of slot (e.g., a generally rectangular slot) that extends through the shoulder of the locking member 33 to receive and retain a portion (e.g., the first end 41) of the energy absorbing member 32. Thus, the shoulder of the locking member 33 may have a generally double-D shaped retention feature to retain the energy absorbing member 32.

For the retractor 20 having the spool assembly 30, the rotation of the spool 31 relative to the locking member 33 is achieved only by overcoming the torque of the energy absorbing member 32 (e.g., the spring). Accordingly, when the retractor 20 is configured in the second or energy absorbing mode of operation, the energy absorbing member 32 (e.g., the spring) absorbs energy (e.g., torque) as the spool 31 is rotated relative to the locking member 33.

The retractor 20 having the spool assembly 30 including the energy absorbing member configured as a torsion spring 32 provides progressive load limiting. During a dynamic vehicle event, the locking member 33 is locked by the actuator and the torsion spring 32 initially provides a relative low level of energy and load (e.g., torque) absorption. Then, as more webbing 12 is extracted (e.g., pays-out) from the retractor 20 as a result of spool 31 rotation induced by occupant loading of the webbing 12 caused by acceleration of the occupant, the spool 31 rotates relative to the locking member 33 thereby winding the torsion spring 32 and increasing the torque necessary to overcome the torsion spring 32 to wind the spring 32 farther. Accordingly, as the torsion spring 32 winds, the torsion spring 32 increases the level of energy (e.g., torque) absorption that the torsion spring 32 and spool assembly 30 absorbs. The spool assembly 30 continues to absorb an increasing level of energy (e.g., torque) as the torsion spring 32 is wound, until the torsion spring 32 reaches a solid state (i.e., where there is no longer any gap between the adjacent coils of the body 40 of the torsion spring 32 as each coil is in full contact with the adjacent coils).

Figure 19:
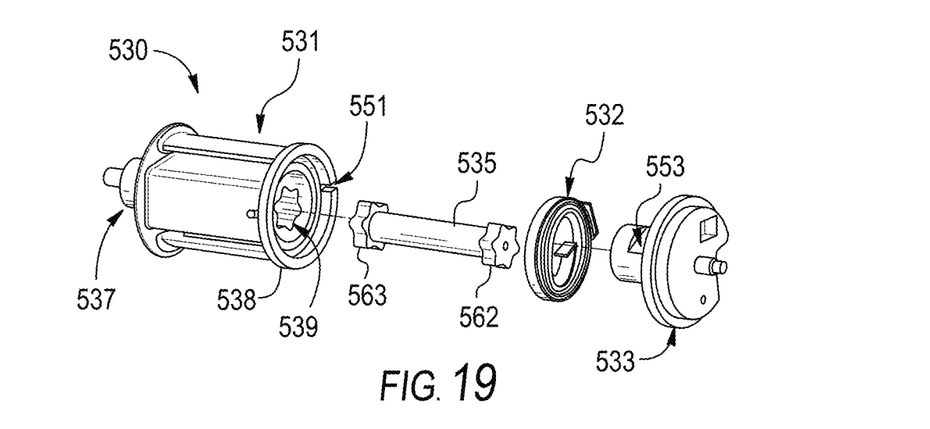
FIG. 19 is an exploded perspective view of yet another exemplary embodiment of a load limiting assembly for use in a retractor.
Figure 20:
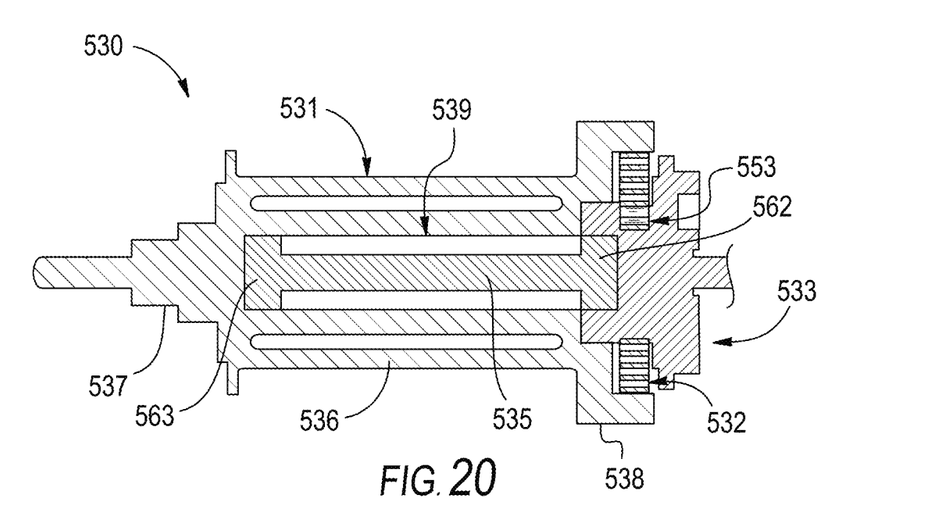
FIG. 20 is a cross-sectional view of the load limiting assembly of FIG. 19.

The retractor 20 may also be configured with more than one energy absorbing member to further tailor the load limiting characteristics of the retractor 20. As shown in FIGS. 19-20, the retractor (e.g., the retractor 20) includes a spool assembly 530 having a spool 531, a first energy absorbing member 535, a second energy absorbing member 532, and a locking member 533. The first energy absorbing member 535 may be configured as a torsion bar, which extends between a first end 537 of the spool 531 and the locking member 533, such as along a longitudinal axis of the spool 531, to transmit torque by absorbing energy when the retractor is locked. Thus, the first energy absorbing member 535 may include a first end 562 and a second end 563. The first end 562 may be configured to engage the first end 537 of the spool 531 to transmit torque therebetween, and the second end 563 may be configured to engage the locking member 533 to transmit torque therebetween. The first energy absorbing member 535 may be disposed in a cavity 539 defined by an inner surface of the annular body 536 of the spool.

The second energy absorbing member 532 may be configured substantially the same as the energy absorbing member 32, such as to absorb energy during relative motion between the spool 531 and the locking member 533. Thus, the energy absorbing member 532 may include a first end that is retained by a retaining feature 551 (e.g., slot), such as in the second end 538 of the spool 531, and may also include a second end that is retained by a retaining feature 553 (e.g., notch) of the locking member 533.

The locking member 533 may be configured substantially the same as the locking member 33, but may also include a key-way feature that is configured to engage and retain the second end 563 of the first energy absorbing member 535 to transmit torque therebetween. For example, the locking member 533 may include a cavity 573 having a key-way feature (e.g., a spline, a star-shape, etc.) that is configured to receive the second end 563, which may be configured having a key-way feature in the form of a complementary or a mating shape (e.g., geometry) as the key-way feature of the locking member 533.

The spool assembly 530 of the retractor (e.g., the retractor 20) may include two (or more) energy absorbing members, such as the first and second energy absorbing members 535, 532, in order to provide, for example, the retractor 20 with a dual-phase load limiting characteristic. The first phase may include a predetermined minimum level of load absorption (e.g., restraint to the webbing 12 and secured occupant) that is based on the strength in torsion of the first energy absorbing member 535 (e.g., the torsion bar) and may, for example, occur prior to loading through the second energy absorbing member 532, such as prior to winding of the torsion spring 532. One or both of the retaining members 551, 553 may be configured to allow a threshold rotation of the spool 531 with respect to the locking member 533 to delay energy absorption by the second energy absorbing member 532 until the threshold is reached. For example, the retaining member 551 may be in the form of an oversized notch that allows the retained end of the spring 532 to rotate a predetermined rotational distance until a wall defining the notch prevents further rotation of the retained end of the spring 532. The second phase may include the progressive load limiting that the second energy absorbing member 532 (e.g., the torsion spring) introduces once the spool 531 begins rotating relative to the locking member 533, such as when the first energy absorbing member 535 (e.g., the torsion bar) yields (e.g., elastically, plastically).

Alternatively, the first and second energy absorbing members 532, 535 may be configured to absorb energy substantially simultaneously. With this arrangement, the retractor may progressively absorb energy from the initial loading of the retractor by having both energy absorbing members absorb energy (and load). In other words, the first phase of the retractor may involve both the first and second energy absorbing members 532, 535 absorbing energy.

Figure 9:
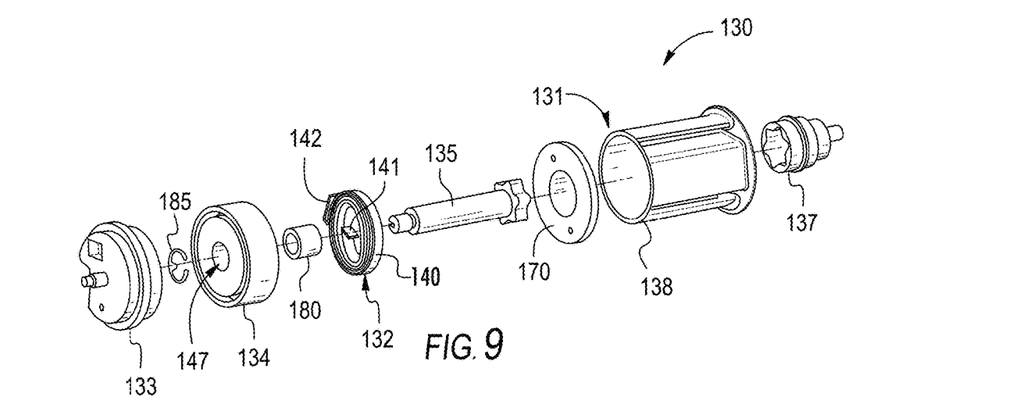
FIG. 9 is an exploded perspective view of another exemplary embodiment of a load limiting assembly for use in a retractor.
Figure 10:
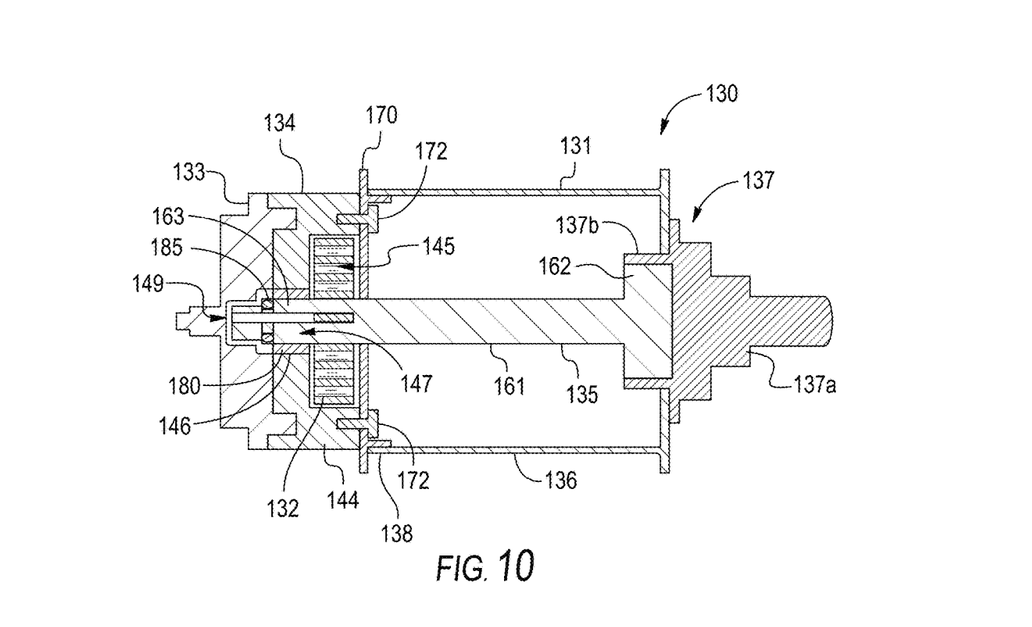
FIG. 10 is a cross-sectional view of the load limiting assembly of FIG. 9.

FIGS. 9 and 10 illustrate another exemplary embodiment of a load limiting spool assembly 130 for use in refractor (e.g., the retractor 20), where the spool assembly 130 is configured to provide a progressive load limiting characteristic for the retractor. The spool assembly 130 includes a spool 131, an energy absorbing member in the form of a spring 132, a locking base 133, a spring case 134 (e.g., spring housing), and a shaft 135. Thus, the retractor may include the spool 131, the spring 132, the locking base 133, a spring case 134 to provide progressive load limiting, and a shaft 135.

The spool 131 includes an annular body 136 that is configured to be coupled to an end of the webbing 12, a first end 137, and a second end 138. The first end 137 includes an outer portion 137a that is configured to engage the frame (e.g., an aperture 27) of the retractor to support the spool 131 and to allow the spool 131 to rotate relative to the frame to wind and unwind the webbing 12 from the retractor. The outer portion 137a may be configured as a shoulder, as more than one shoulder as shown, may be configured as a bearing, or may have any suitable shape that allows for efficient rotation of the spool 131 relative to the frame of the retractor. The first end 137 also includes an inner portion 137b that is configured to receive and support the shaft 135. The inner portion 137b is shown in the form of a carriage 137b that includes a female key-way shape (e.g., spline, star, etc.) that is configured to receive and retain a corresponding male key-way shaped portion of the shaft 135 to prohibit relative rotation of the shaft 135 relative to the spool 131. In other words, the first end 162 of the shaft 135 is configured to engage and transmit torque to the inner portion 137b. However, the inner portion 137b may be formed having any shape suitable that receives and transmits torque from the shaft 135. The second end 138 of the spool 131 may be configured to receive the spring case 134 or a spring cover 170, if provided. In other words, the spring case 134 may be pivotally coupled directly to the second end 138 of the spool 131, such as to retain the spring 132 therebetween, or a spring cover 170 may be disposed between the spring case 134 and the second end 138 of the spool 131, such as to support the shaft 135 and/or to retain the spring 132 in the spring case 134. Accordingly, for the retractor having the spring cover 170, the spring cover 170 may be pivotally coupled to the spool 131, such as the second end 138, and may be operatively coupled to the spring case 134.

The spring 132 is configured to absorb energy in a progressive manner from a threshold level as the spring 132 is wound about a pivot axis, which may extend longitudinally through the spool assembly 130. The spring 132 may be configured as a torsion spring, such as described above for spring 32, having a body 140 in the form of a coil that absorbs energy (e.g., torque, load, etc.), a first tang 141 (e.g., first end), and a second tang 142 (e.g., second end). The first end 141 may extend from an end of the inner coil of the body 140 that is centrally located, and the second end 142 may extend from an end of the outer coil of the body 140 that is located on the periphery of the body 140. The spring 132 is configured to provide energy and load absorption as the spring 132 is wound and/or unwound (i.e., one end is rotated relative to the other end), whereby the level of energy and load absorption is a function of the spring rate of the spring 32, as well as the rotational travel of the spring (e.g., one end relative to another end).

The spring case 134 is disposed on the second end 138 (or at the second end 138 for the retractor having the spring cover 170) of the spool 131 to retain the spring 132 in position longitudinally along the pivot axis relative to another component (e.g., the spool 131) of the spool assembly 130. The spring case 134 includes a body 144 having a cavity 145 (e.g., bore) that is configured to house the spring 132 therein. The body 144 may be configured to be pivotally coupled directly to the body 136 of the spool 131 or may be configured to be coupled directly to the spring cover 170, if provided, where the spring cover 170 may be pivotally coupled to the spool 131. The body 144 may include a retention feature (not shown), such as a hook or tab, that may protrude into the cavity 145, whereby the retention feature is configured to receive and retain a portion of the spring 132, such as the second end 142, to thereby prevent relative rotation of the second end 142 relative to the retention feature of the spring case 134. The retention feature of the body 144 may be configured as a notch, a channel, or a slot, which retains the spring 132 to prevent relative rotation between the second end 142 and the spring case 134.

The spring case 134 may include a bearing surface 146, such as if a bearing 180 is provided between the shaft 135 and the spring case 134. The bearing surface 146 may be defined by an opening or second bore 147 that extends through the body 144 of the spring case 134. The second bore 147 allows the shaft 135 to pass therethrough, such that the bearing surface 146 may support the shaft 135 in the second bore 147, either directly or indirectly through the bearing 180.

Figure 15:
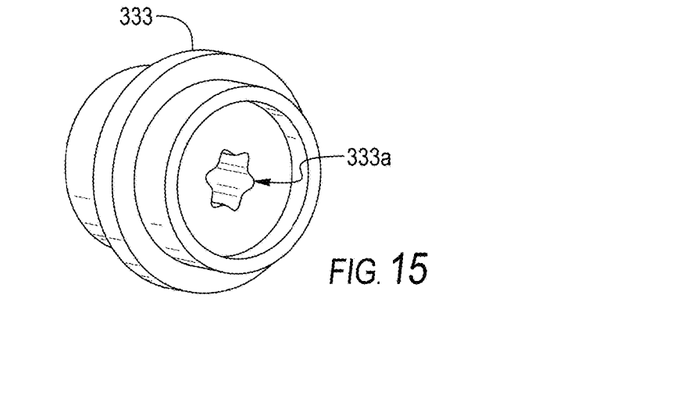
FIG. 15 is a perspective view of the locking member of the load limiting assembly of FIG. 13.

As shown in FIG. 10, the locking base 133 (e.g., locking member) is disposed adjacent to the spring case 134 on the side opposing the spool 131. The locking base 133 is operatively coupled to the spring case 134, such that the locking base 133 and the spring case 134 are able to rotate together relative to the spool 131 in order to wind the spring 132 upon relative rotation between the spool 131 and the locking base 133. The locking base 133 may also include a recess 149 configured to receive a portion of the shaft 135. The recess 149 may be a generally cylindrical shaped bore that is configured to receive the bearing 180. Alternatively, the recess may have a key-way shape that is configured to receive an end of the shaft to transmit torque between the shaft and the locking base, as shown in the example of FIG. 15.

The locking base 133 may also be pivotally coupled to the frame 24 of the retractor and configured to be selectively engaged by an actuator (not shown) to prevent rotation of the locking base 133 relative to the frame 24. The locking base 133 is configured to operate in two modes of operation, a first (e.g., free) mode of operation and a second (e.g., energy absorbing) mode of operation, which correspond to the two modes of operation of the retractor. When in the first mode of operation (e.g., free mode), the actuator does not engage the locking base 133 and the locking base 133 is allowed to freely rotate relative to the frame, such that the locking base 133 and the spool 131 may rotate together to wind and unwind the webbing 12 from the retractor. When in the second mode of operation (e.g., the energy absorbing mode of operation), the actuator is activated to thereby engage and lock the locking base 133 to prevent rotation of the locking base 133 relative to the frame 24. In the second mode of operation, the spool 131 is allowed to rotate in the webbing extracting direction relative to the locking base 133 only as energy is absorbed by the spring 132 and/or the shaft 135 (depending on the arrangement of the retractor).

The shaft 135 is operatively coupled to the spool 131. The shaft 135 includes a body portion 161, a first end 162, and a second end 163 The first end 162 may have a male key-way shape that engages a mating female key-way shape of the inner portion 137b of the first end 137 of the spool 131 to thereby prohibit relative rotation of the first end 162 of the shaft 135 relative to the spool 131. Accordingly, torque input into the spool 131 is transmitted (e.g., communicated, transferred, etc.) to the shaft 135 through the first end 162. The second end 163 may include a retention feature configured to retain a portion of the spring 132, such as the first end 141 (e.g., inner end) of the spring 132. For example, the second end 163 may include a notch (e.g., a channel) that is configured to receive the first end 141 of the spring 132. The notch may extend at a length along the longitudinal direction of the shaft, and the length may be tailored to accommodate the desired lateral position of the spring 132. Accordingly, with the second end 142 (e.g., outer end) of the spring being retained by the spring case 134, relative rotation between the spool 131 and the locking base 133 transfers load and energy into the spring 132, since rotation of the spool 131 relative to the locking base 133 is achieved only by overcoming the torque of the spring 132. Accordingly, when the retractor 20 is configured in the second or energy absorbing mode of operation, the spring 132 absorbs load and energy (e.g., torque) as the spool 131 is rotated relative to the locking member 133.

Figure 13:
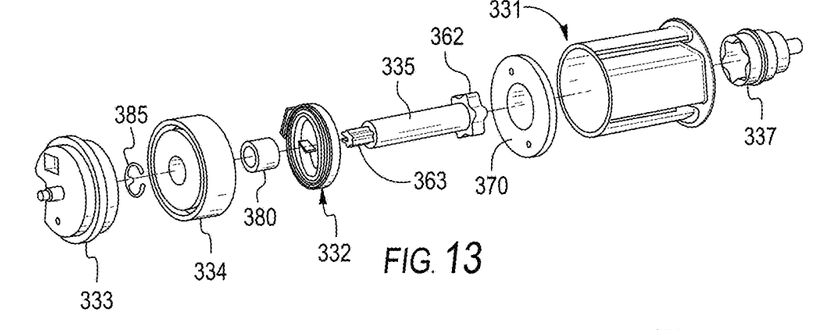
FIG. 13 is an exploded perspective view of another exemplary embodiment of a load limiting assembly for use in a retractor.
Figure 14:
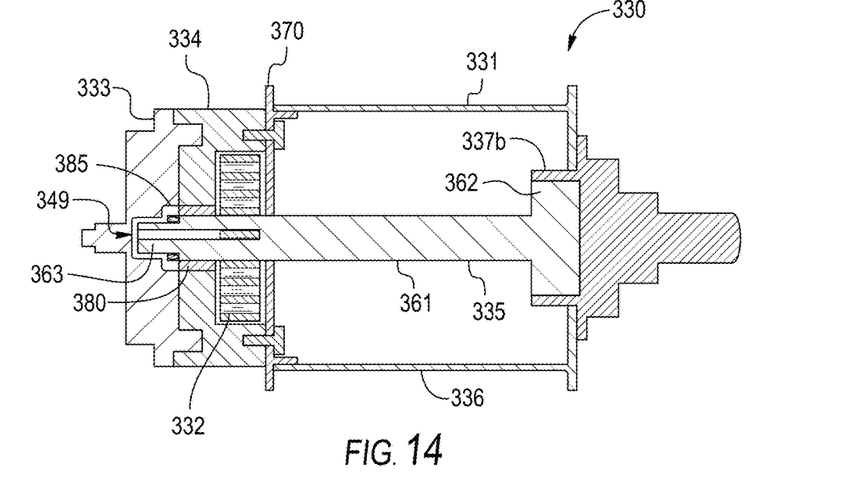
FIG. 14 is a cross-sectional view of the load limiting assembly of FIG. 13.

The shaft 135 may be configured as an energy absorbing member, such as a torsion bar, where both the first and second ends 162, 163 are configured to thereby transfer (e.g., transmit, communicate, etc.) torque from one end to the other through the body 161 of the shaft 135. As shown in FIGS. 13 and 14, the energy absorbing member 335 of the spool assembly 330 includes a first end 362 that transfers torque to (and from) the spool 331 and a second end 363 that transfers torque to (and from) the locking base 333. For example, the second end 363 of the energy absorbing member 335 may have a key-way (e.g., male key-way) that engages an opening 333a (e.g., recess, cavity, etc.) having a complementary or mating key-way (e.g., female key-way) in the locking base 333 to operatively couple (e.g., transfer torque between) the energy absorbing member 335 and the locking base 333. Also, for example, the first end 362 of the energy absorbing member 335 may include a key-way, such as the key-way discussed above for the first end 162 of the shaft 135, that engages an inner portion 337b having a complementary or mating key-way in the first end 337 of the spool 331 to operatively couple the energy absorbing member 335 and the locking base 333. Accordingly, when in the energy absorbing mode of operation, the body 361 of the shaft 335 transfers or absorbs a predetermined amount of torque, such as a torque generated by the force exerted by the extracting webbing 12 that is being loaded by the force of an occupant being accelerated during a dynamic vehicle impact event. The body 361 may provide energy management by transferring or absorbing the predetermined torque first through elastic deformation, then through plastic deformation.

The spool assembly 330 of FIGS. 13 and 14 may also include an additional energy absorbing, such as, for example, in the form of a spring 332, a spring case 334, a spring cover 370, a bearing 380, and/or a retaining member 385, which may be configured substantially the same as or different than the spring 132, the spring case 134, the spring cover 170, the bearing 180, and/or the retaining member 185. The locking base 333 may also include a cylindrical shaped bore 349 that is configured to house a portion (e.g., a shoulder) of the second end 363 and the retaining member 385, if provided. For example, as shown in FIG. 15, the locking base 333 may include an opening 333a having a complementary shape to the shape of the second end 363 to transfer torque between the locking base 333 and the energy absorbing member 335.

As shown in FIGS. 9 and 10, the spool assembly 130 may also include a spring cover 170 that is disposed between the spool 131 and the spring case 134 to help retain the spring 132 in place, such as in the cavity 145 formed in the spring case 134. The spring cover 170 may have a flat shape or any suitable shape. The spring cover 170 may be configured to cover at least a portion of the spring 132, such as to limit the lateral movement (e.g., in the longitudinal direction) of the spring 132 along the shaft 135 to help retain the first and second ends 141, 142 of the spring 132 by the retention features of the shaft 135 and the spring case 134. The spring cover 170 may be coupled to the spring case 134 through any suitable method, such as by fasteners 172 (e.g., screws) that clamp the spring cover 170 to the spring case 134.

The spool assembly 130 may also include a bearing 180. The bearing 180 may be integrally formed with the spring case 134, or may be formed separately and assembled within a bearing surface 146 of the spring case 134. As shown, the bearing 180 is configured as a journal bearing that supports a portion of the second end 163 of the shaft 135 to allow constrained relative rotation between the spring case 134 and the shaft 135. It is noted that the bearing 180 may be configured as a sleeve bearing or any suitable bearing that allows efficient relative rotation between the shaft 135 and the spring case 134.

The spool assembly 130 may also include a retaining member 185, such as shown in FIGS. 9 and 10 in the form of an E-ring 185. The E-ring 185 may be configured to engage the second end 163 of the shaft 135, such as a groove in the second end 163, whereby the E-ring 185 limits movement of the shaft 135 along its longitudinal axis relative to the spring case 134 and the locking base 133. For example, the E-ring 185 may be disposed between the locking base 133 and the spring case 134 to thereby prevent the E-ring 185 from being able to move beyond the contacted locking base 133 and spring case 134, which in turn limits the movement of the shaft 135 in the same directions.

Figure 11:
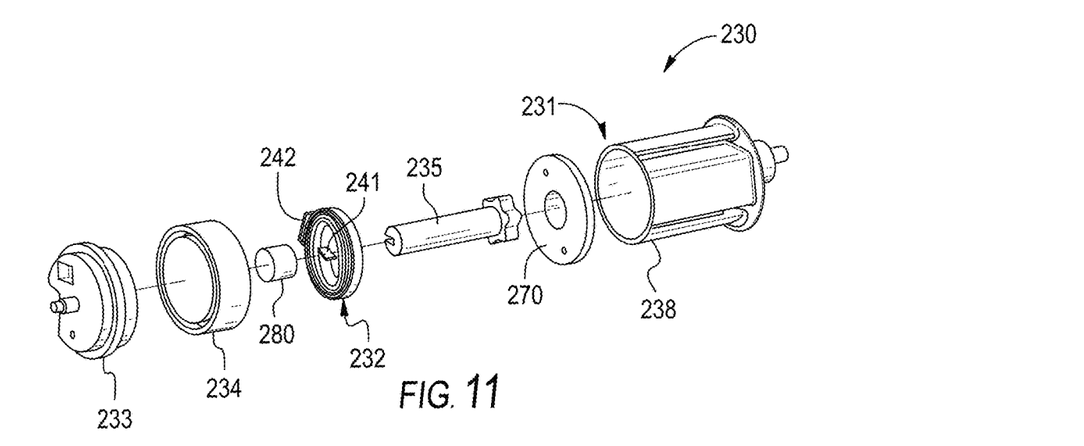
FIG. 11 is an exploded perspective view of another exemplary embodiment of a load limiting assembly for use in a retractor.
Figure 12:
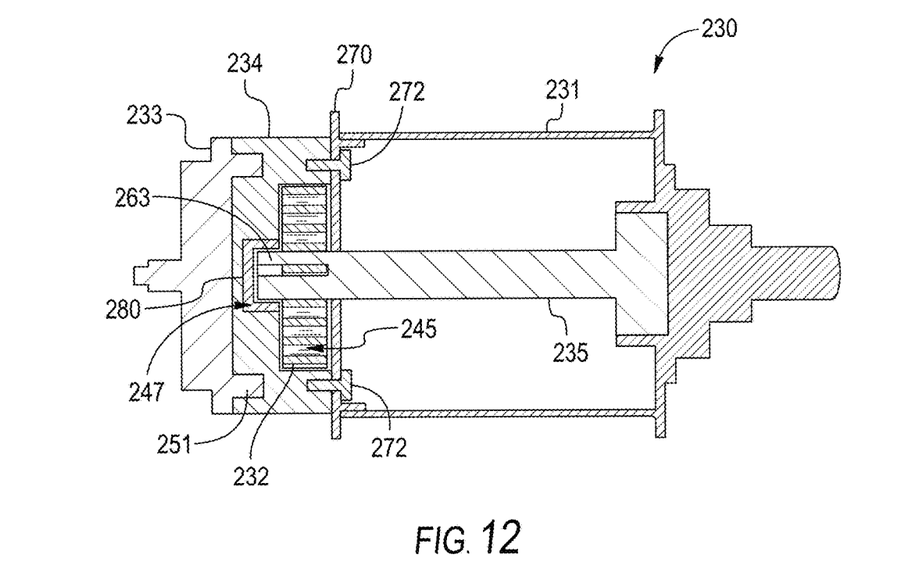
FIG. 12 is a cross-sectional view of the load limiting assembly of FIG. 11.
Figure 16:
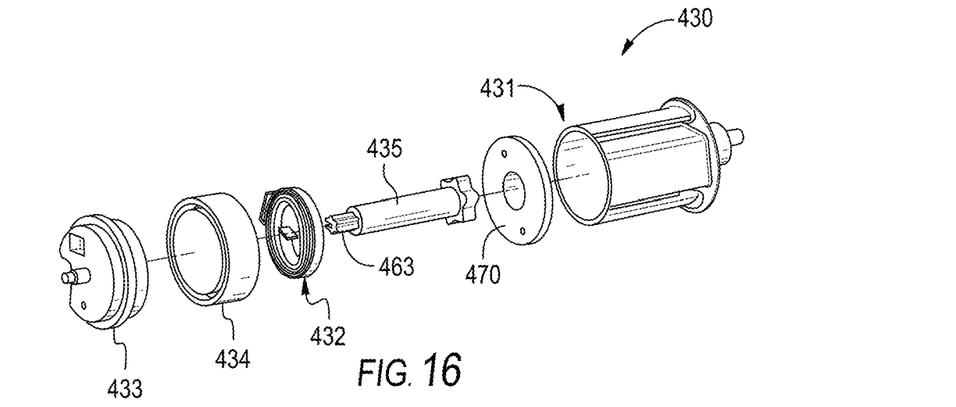
FIG. 16 is an exploded perspective view of another exemplary embodiment of a load limiting assembly for use in a retractor.
Figure 17:
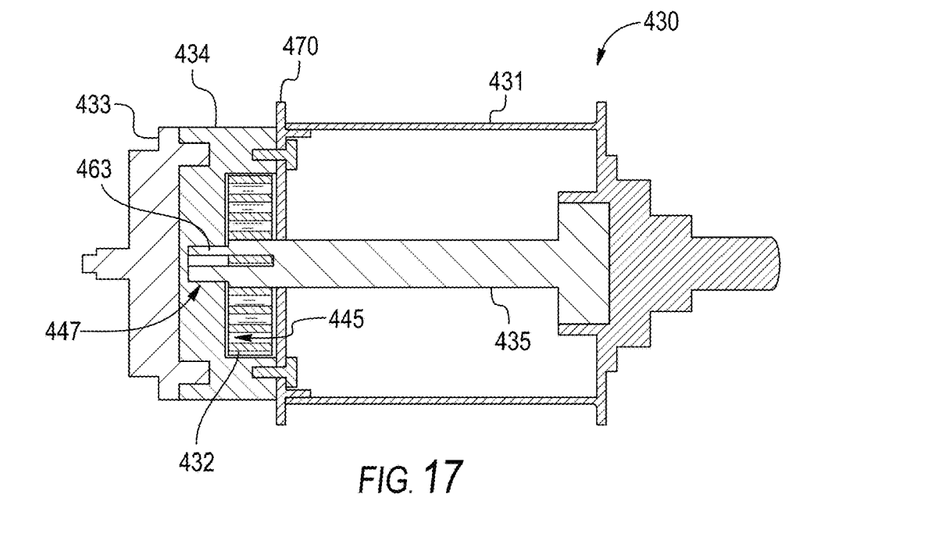
FIG. 17 is a cross-sectional view of the load limiting assembly of FIG. 16.

FIGS. 11 and 12 illustrate another exemplary embodiment of a load limiting spool assembly 230 that is configured to provide a progressive load limiting characteristic. FIGS. 16 and 17 illustrate another exemplary embodiment of a load limiting spool assembly 430 that is a modified version of the spool assembly 230 in order to provide a dual-phase progressive load limiting retractor. As shown in FIGS. 11 and 12, the spool assembly 230 includes a spool 231, a spring 232, a locking base 233, a spring case 234, and a shaft 235. The spool assembly 230 may also include a spring cover 270. The spool 231, the spring 232, and the spring cover 270 may be configured as disclosed above, such as, for example, being generally the same as the spool 131, the spring 132, and the spring cover 170, respectively. For example, the spring 232 may include a first end 241 and a second end 242, where the first end 241 is configured to be retained or coupled to a first component (e.g., the shaft 235) of the spool assembly 230, and where the second end 242 is configured to be retained or coupled to a second component (e.g., the spring case 234).

The shaft 235 may be configured as disclosed above, for example, for the shaft 135, except the shaft 235 is shorter in length, such that a second end 263 of the shaft 235 extends into a bearing 280 that is disposed between the spring case 234 and the second end 263. Alternatively, the second end 263 may extend into a sub-cavity 247, such as if no bearing 280 is provided and/or when the shaft 235 is configured as a torsion bar having a second end 263 configured to transfer torque between the spring case 234 and the shaft 235.

As shown, the spring case 234 includes a cavity 245 provided on the side that is adjacent to (e.g., faces toward) the shaft 235, where the cavity 245 is configured to receive and house the spring 232 therein. The cavity 245 may be in the form of a bore having a cylindrical shape, where the depth of the bore is at least as long as the width (e.g., thickness) of the spring 232 to allow the spring cover 270 to sit flush or inwardly offset from with the side of the spring case 234 that faces the spool 231 or the spring cover 270, if the spring cover 270 is provided in the spool assembly 230. One or more than one fastener 272 may couple the spring cover 270, if provided, to the spring case 234. The cavity 245 may include a sub-cavity 247 configured as a second bore that extends in the direction away from the spool 231 relative to the cavity 245 that houses the spring 232. The sub-cavity 247 is configured to receive and house the bearing 280, which allows constrained relative rotation between the shaft 235 and the spring case 234, such as when the spool assembly 230 is configured in the energy absorbing (or locked) mode of operation. The sub-cavity 247 may have, for example, a cylindrical shape with a diameter that is smaller relative to the size (e.g., diameter) of the cavity 245. Alternatively, the sub-cavity 247 may be configured to receive the second end 263 of the shaft 235, such as where the sub-cavity 247 may have a key-way that complements a mating key-way of the second end 263.

Figure 18:
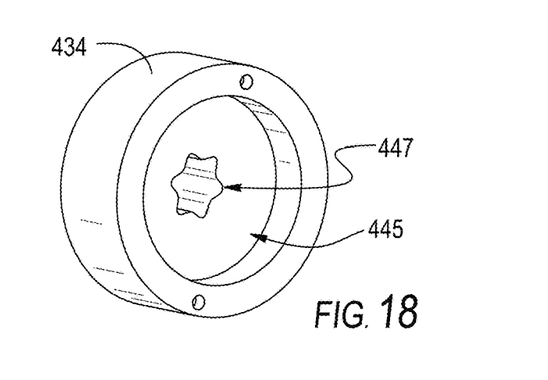
FIG. 18 is a perspective view of the case of load limiting assembly of FIG. 16.

As shown in FIGS. 16-18, the spool assembly 430 includes a spring case 434 having a first cavity 445 configured to receive the spring 432 and a second cavity 447 extending from the first cavity 445 to receive the second end 463 of the shaft 435. The first cavity 445 may be configured generally the same as the cavity 245, and the second cavity 447 may be in the form of a generally star-shaped key-way that is configured to receive a mating generally star-shaped second end 463 to allow torque to be transferred between the shaft 435 and the spring case 434. Thus, the shaft 435 may absorb energy when the spool 431 rotates relative to the spring case 434, such as during loading of the webbing of the seat belt when the locking base 433 is locked. The spool assembly 430 may also include a spring cover 470 that is disposed between the spring case 434 and the spool 431.

As shown in FIG. 12, the bearing 280 may be ferrule shaped having a generally C-shaped cross-section to support the second end 263 of the shaft 235 and to fit within the sub-cavity 247 of the spring case 234. Accordingly, the bearing 280 is disposed between the spring case 234 and the second end 263 of the shaft 235 to allow for relative rotation therebetween.

As shown, the locking base 233 may be configured as disclosed above for the locking base 133, except without a recess on the side facing the spring case 234. Since the shaft 235 extends only to the spring case 234 and not to the locking base 233, the locking base 233 does not require a recess to house a portion of the shaft 235 (e.g., the second end 263) therein. The locking base 233 may include connections 251, such as, for operatively coupling or connecting the locking base 233 to the spring case 234. For example, the connections 251 may be configured as locking tabs that extend into apertures in the spring case 234 to couple the locking base 233 to the spring case 234.

FIG. 21 is a graph showing the load over the deflection for several embodiments of retractors having various configurations that provide varying levels of energy management, such as to a secured occupant during a dynamic vehicle impact event. As shown, the retractor having just a torsion bar provides a single level of load and energy absorption, once the predetermined load level is reached. Also, as shown, the retractor having a digressive load limiter (DLL) starts off absorbing a first level of load and energy, then after a predetermined number of rotations by the spool of the retractor, shifts or switches to a relative lower level of load and energy absorption. In contrast to these, the retractor having with a progressive load limiter (PLL), such as the spool assemblies disclosed herein, may start off managing a first level of load and energy, then as more webbing is extracted (e.g., unwound) from the retractor, the PLL progressively increases the level of load and energy management, such as from the spool winding the energy absorbing member (e.g., spring) relative to the locking base or member. Additionally, the PLL provides a steadily increasing level of load and energy management, until, for example, the torsion spring reaches its solid state, whereby the load and energy management may plateau or rise very rapidly depending on the compliance of the system. This arrangement may be beneficial, as it provides a hard stop to thereby prevent additional extraction of the webbing from the retractor to thereby limit the deflection of the secured occupant to a predetermined and repeatable amount of deflection. The slope at which the PLL absorbs load and energy may be varied, such as by modifying the spring rate of the energy absorbing member. The PLL being mechanical in nature allows for the retractors having the PLL spool assemblies, as disclosed herein, to be easily modified to tailor the performance characteristics of the retractors, and also provides repeatable performance from retractor to retractor having a similar configuration.

The retractors disclosed above may also include a catch feature that may be configured to retain the load subjected to the energy absorbing member (e.g., spring) during and after the dynamic vehicle event. Accordingly, the catch feature may prevent back-winding (e.g., retraction) of the webbing into the retractor during and after the vehicle event. If the spool assembly includes both a energy absorbing member and a torsion bar, the catch feature may not be necessary, as the plastic deformation of the torsion bar may prevent back-winding of the webbing into the retractor.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of the retractors as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present invention.

According to an exemplary embodiment a seat belt retractor is provided that includes: a spool configured to wind and unwind a seat belt webbing; a locking base; and an energy absorbing member having a first end operatively connected to the locking base and a second end operatively connected to the spool; wherein the energy absorbing member provides a progressive level of load resistance upon relative rotation between the spool and the locking base. The retractor may further include a case disposed between the locking base and the spool, the case being operatively coupled to the locking base and configured to house the energy absorbing member. Also, the seat belt retractor may include a torsion bar configured to transfer torque between the spool and the operatively coupled locking base and case, wherein the torsion bar provides a first level of load resistance and the energy absorbing member provides a second progressive level of load resistance upon relative rotation between the spool and the locking base.

What is claimed is:

1. A retractor assembly for a seatbelt system having a webbing for restraining a secured occupant, the retractor comprising:
   a spool configured to wind and unwind the webbing;
   a locking base including a shoulder engaging a cavity of the spool, wherein the locking base is configured to selectively lock the spool; and
   an energy absorbing member having a first end directly connected to the locking base, such that the first end is fixed relative to the locking base, and a second end directly connected to the spool, such that the second end is fixed relative to the spool;
   wherein the energy absorbing member provides a progressive level of load resistance upon relative rotation between the spool and the locking base.

2. The refractor of claim 1, wherein the energy absorbing member is disposed in the cavity of the spool between the locking base and an end of the spool, such that an outer tang of the energy absorbing member engages a slot in the end of the spool and an inner tang of the energy absorbing member engages an undercut portion in a shoulder of the locking base.

3. The refractor of claim 1, further comprising a torsion bar configured to transfer torque between the spool and the locking base, wherein the torsion bar includes a first member and a second member, wherein the first member is directly connected to the spool, such that torque from the spool is transmitted directly to the first member, and wherein the second member is directly connected to the locking base, such that torque from the torsion bar is transmitted directly to the locking base.

4. The refractor of claim 3, wherein the torsion bar provides a first level of load resistance and the energy absorbing member provides a second progressive level of load resistance upon relative rotation between the spool and locking base, wherein the first level includes a uniform load for a first time, and wherein the second progressive level is after the first level and progressively increases in load from the uniform load for a second time.

5. The refractor of claim 1, wherein the energy absorbing member is a spring including a body, an outer tang, and an inner tang, wherein the body is disposed in a space provided between an inner surface of the spool and an outer surface of the locking base, wherein the outer tang is fixed to the spool and the inner tang is fixed to the locking base.

6. The retractor of claim 5, wherein the spring is a torsion spring and the inner tang is fixed in a notch in the outer surface of the locking base, and wherein the outer tang is fixed in a slot extending from the inner surface to an outer surface of the spool.

7. A retractor assembly for a seatbelt system having a webbing for restraining a secured occupant, the retractor comprising:
   a spool configured to wind and unwind the webbing;
   a lock base;
   a shaft disposed in a cavity defined by an inner surface of the spool, the shaft having a first end directly connected to the lock base and a second end directly connected to the spool; and
   an energy absorbing member having a first end directly connected to the lock base and a second end directly connected to the spool, wherein the energy absorbing member does not engage the shaft;
   wherein the energy absorbing member provides a progressive level of load resistance upon relative rotation between the spool and lock base.

8. The retractor of claim 7, wherein the shaft is a second energy absorbing member that is configured to provide a uniform level of load resistance upon relative rotation between the spool and lock base for a first time, wherein the first end is fixed relative to the lock base, and wherein the progressive level of load resistance from the energy absorbing member is after the uniform level and progressively increases in load from the uniform load for a second time.

9. The retractor of claim 8, wherein the first end of the shaft is operatively coupled to a shoulder of the lock base through complementary key-way features.

10. The retractor of claim 7, wherein the energy absorbing member is disposed in the cavity of the spool between an outer surface of the lock base and the inner surface of the spool, wherein the energy absorbing member is directly connected to a shoulder of the lock base via an inner tang extending away from a body of the energy absorbing member, and wherein the energy absorbing member includes an outer tang that is directly connected to the spool.

11. The retractor of claim 10, wherein the cavity of the spool includes a first portion, a second portion and a third portion, wherein the shaft is disposed in the first portion of the cavity, wherein the second portion of the cavity is configured to receive the shoulder of the lock base, and wherein the third portion of the cavity is configured to receive the energy absorbing member therein.

12. The retractor of claim 11, wherein the first portion of the cavity has a key-way shape that complements a key-way shape of the second end of the shaft, wherein the second portion of the cavity has an inner diameter that receives the shoulder of the lock base, and wherein the third portion includes an inner diameter that houses the energy absorbing member.

13. The retractor of claim 12, wherein the inner diameter of the second portion of the cavity is smaller than the inner diameter of the third portion of the cavity.

14. The retractor of claim 13, wherein the shoulder of the lock base includes an opening that receives the first end of the shaft, wherein the opening is configured as a key-way that complements the shape of the first end of the shaft.

15. The retractor of claim 7, wherein the lock base includes a cavity that engages the first end of the shaft, wherein the cavity and the first end have mating shapes that transmit torque therebetween.

16. A retractor assembly for a seatbelt system having a webbing for restraining a secured occupant, the retractor comprising:
   a spool configured to wind and unwind the webbing about an axis;
   a lock base;
   a first energy absorbing member extending along the axis, the first energy absorbing member having a first end operatively connected to a cavity in an end of a shoulder of the lock base and a second end operatively connected to a cavity in a first end of the spool; and
   a second energy absorbing member having a first end operatively connected to the shoulder of the lock base and a second end operatively connected to the a second end of the spool;
   wherein upon relative rotation between the spool and locking base, the first energy absorbing member provides a first level of load resistance and the second energy absorbing member provides a progressive level of load resistance.

17. The retractor of claim 16, wherein the first end of the first energy absorbing member is directly connected to the shoulder of the lock base, wherein the second end of the first energy absorbing member is directly connected to the spool, wherein the first end of the second energy absorbing member is directly connected to the shoulder of the lock base, and wherein the second end of the second energy absorbing member is fixedly connected in a slot in the second end of the spool.

18. The retractor of claim 17, wherein the outer surface of the shoulder includes a notch to fixedly connect the first end of the second energy absorbing member to the shoulder of the lock base, and wherein the second energy absorbing member is a torsion spring that absorbs energy when wound about the axis.

19. The retractor of claim 16, wherein the second energy absorbing member is disposed in a cavity in the second end of the spool, such that the second end of the spool encloses a body of the second energy absorbing member, wherein the first level of load resistance includes a uniform load for a first time, and wherein the second progressive level of load resistance is after the first level and progressively increases in load from the uniform load for a second time.

20. The retractor of claim 16, wherein the spool includes an inner shoulder disposed between the cavities in the first and second ends of the spool, wherein the shoulder of the lock base is pivotally coupled to the inner shoulder of the spool, such that the spool rotates relative to the lock base when in an unlocked position and the spool and lock base rotated together when in a locked position.

\* \* \* \* \*